United States Patent [19]

Holmberg

[11] 4,177,668
[45] Dec. 11, 1979

[54] APPARATUS FOR DETERMINING THE ALCOHOLIC CONTENT IN THE BLOOD

[76] Inventor: Lars-Erik Holmberg, Box 184, S-201 21 Malmö, Sweden

[21] Appl. No.: 902,050

[22] Filed: May 2, 1978

[30] Foreign Application Priority Data

May 4, 1977 [SE] Sweden .................................. 7705196

[51] Int. Cl.² .......................................... G01N 27/04
[52] U.S. Cl. ...................................... 73/23; 128/719
[58] Field of Search ...................... 73/23, 27, 421.5 R; 128/2 C; 340/332, 634, 576, 660

[56] References Cited

U.S. PATENT DOCUMENTS 3,823,601 7/1974 Hoppesch ................................. 73/23
3,877,291 4/1975 Hoppesch et al. ........................ 73/27

Primary Examiner—Charles A. Ruehl

[57] ABSTRACT

An apparatus for determining the alcoholic content in blood. A sensor receives exhaled air from a person being tested and produces a signal which is sent to at least two comparator devices for comparing the output signal with at least two preset reference values. A logic circuitry of TTL elements is connected to the output of the comparator device and is arranged in conjunction with three light emitting diodes to actuate at least one light emitting diode based upon the result of the comparison to thereby indicate the alcoholic content. A first light emitting diode is actuated when the output is below the first reference value, the first light is extinguished and the second light is ignited when the output is between the first and second reference values, and the third light is ignited and the second is extinguished when the output exceeds the second reference value.

14 Claims, 1 Drawing Figure

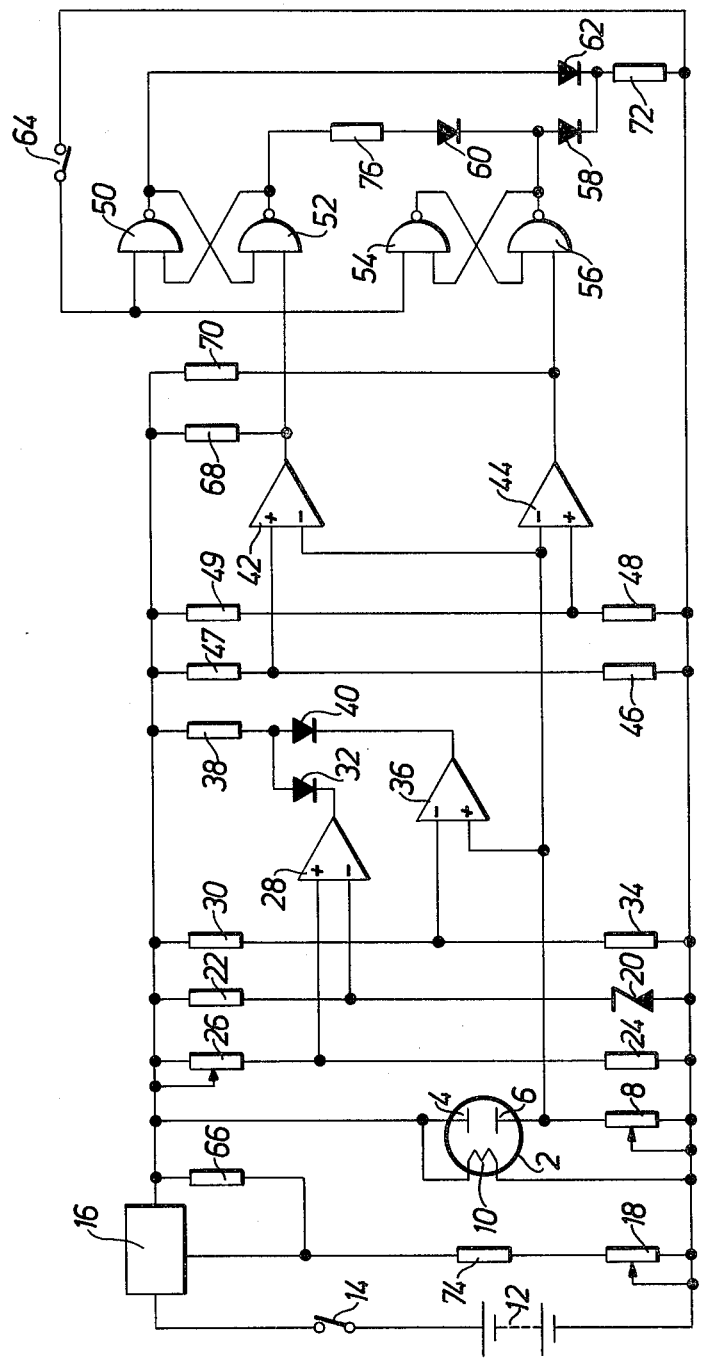

… … …

APPARATUS FOR DETERMINING THE ALCOHOLIC CONTENT IN THE BLOOD

The present invention relates to an apparatus for determining the alcoholic content in the blood, comprising a sensor, which is disposed to provide a signal in response to the alcoholic content in exhalation air, to which it is exposed from a test person, and at least two comparator devices for comparing said output signal with at least two preset reference values.

Alcohol meters of various kinds are previously known. Thus, in the Swedish Patent No. 73 17279-3 a breath testing apparatus is described, which provides a passing indication ("pass"), if the air content in the breath of the test person lies within a predetermined interval. At alcoholic contents exceeding the upper limit of the interval the concentration is too high for a "pass" indication to be permitted and at alcoholic concentrations below the lower limit of the interval some kind of "cheating" will probably be present, so that neither in this case a "pass" indication is obtained. The apparatus is intended to be used without supervision, e.g. in an arrangement together with clutches in motor cars, whereby the driver must exhale air into the testing apparatus in order to obtain a "pass" indication before the car can be driven. The apparatus is then specially designed to impede or prevent any attempt to evade the test. The device according to said patent comprises one single indicator member—a lamp—which is lighted to provide a "pass" indication, if the alcoholic content detected lies within the predetermined interval, or remains extinguished otherwise. As comparator circuits operational amplifiers are utilized and for driving the lamp logic circuits of CMOS type, a transistor stage, and a separate voltage source of 8V.

The Swedish patent application 73 11055-3 relates to a breath tester for alcoholic tests of the "screening type". The device is portable and is intended for use by traffic policemen in the street or on the road in order to perform breath tests at the roadside so as to obtain a basis for release or retention of a car driver for more complicated tests. The device disclosed in said application comprises a sensor element, which provides an output voltage, indicating the alcoholic content in the breath of the test person. Depending on the value of said output signal one of three indicating members are lighted. In order to produce this operation the device comprises two Zener diodes with different breakdown voltages connected to the sensor element. The Zener diodes are each connected to a rectifier and each rectifier in its turn is connected to a light emitting diode for ignition thereof upon a breakdown in the corresponding Zener diode. Also in this device a separate voltage source is required (+12 V in the embodiment according to FIG. 4A in the application) for driving the indicating members.

The object of the present invention is to provide an apparatus for measuring the alcoholic content in the blood, said apparatus being intended for use by private persons, e.g. as an aid for car drivers in order to determine, whether they should drive or not. Another object of the invention is to construct the apparatus so that it will indicate within which one of at least three calibrated concentration intervals the alcoholic content lies. A further object of the invention is to provide an accurate and reliable apparatus with the simplest possible construction.

These objects are achieved by a device of the kind mentioned above which is characterized in that a logic circuitry of TTL elements, connected to the outputs of the comparator devices, is arranged to actuate at least one light emitting diode of a plurality of light emitting diodes, or indicating the alcoholic content, said actuated light emitting diode being determined by the result of said comparison.

By using TTL logic instead of CMOS logic as in the device according to the above Swedish patent No. 73 17279-3, said TTL logic being disposed to drive light emitting diodes arranged as indicator members, the important advantage is achieved that a separate voltage source for supplying the indicator members is not required, since the TTL circuits allow a considerably larger current than CMOS circuits and since light emitting diodes take much less current than a lamp, which is utilized as indicator member in the mentioned prior device. By using light emitting diodes instead of conventional lamps the total driver circuit for the indicator members may be simplified considerably due to the reduced current consumption.

In one advantageous embodiment the logic circuitry comprises two SR flip-flops, each consisting of two NAND gates. Then the complete logic circuitry is preferably realized by means of one single integrated circuit.

According to another preferred embodiment only one voltage source is arranged to provide all necessary feeding voltages to the apparatus, whereby the design thereof is simplified.

A further advantage of the apparatus according to the invention is that it can be calibrated by the output signal from the sensor being taken from a potentiometer or an adjustable resistor connected in series with the sensor, and by the reference voltages required for the comparator devices being taken via adjustable voltage dividing resistors or potentiometers. The reference voltages may then e.g. be set so that the first reference value corresponds to an alcoholic content in the blood of 0.03% and the second reference value to an alcoholic content of 0.05%.

The voltage supply may further be performed via a regulating circuit connected to the voltage source, since it is of great importance that a constant feeding voltage is obtained independent of the condition of the batteries. A first control circuit is then preferably arranged to sense the output voltage from the regulating circuit and indicate, when said voltage has decreased below a predetermined level.

For a correct result it is also of great importance that the sensor is heated to operating temperature before its use is started. For this purpose, according to a preferable embodiment of the invention, a second control circuit is disposed to indicate, when the sensor is heated.

Further, in order to obtain a design as compact and reliable as possible all comparator devices of the apparatus are preferably realized by means of one integrated circuit.

Additional advantages of the device according to the invention will be obvious from the following detailed description of an exemplary embodiment which is shown on the accompanying drawing.

The sensor member or the sensor 2 in the embodiment of the invention illustrated on the drawing is a so-called gas sensor of type Figaro TGS 812. When the sensor is influenced by alcohol in the exhaled air from a test person, the resistance is changed and thereby the current flow between the electrodes 4 and 6 of the sensor, whereby an output voltage is obtained across the potentiometer 8, which voltage varies in response to the alcoholic content in the exhaled air.

For a correct operation it is necessary that the sensor be heated, before it is used. This is performed by means of a built-in heating coil 10. Before the sensor has reached the operating temperature, the resistance first decreases, whereafter it then again increases, and when the resistance then has increased to a certain level, the sensor is ready for use.

The resistance between the electrodes 4 and 6 of the sensor decreases, when it is exposed to air containing alcohol and this change of resistance is thus sensed as a change of voltage across the potentiometer 8. A decreasing sensor resistance causes an increasing voltage across the potentiometer 8. If the driving voltage of the sensor 2 is maintained constant, it is possible to calibrate the sensor by measuring the voltages which some given alcoholic contents in blood (e.g. 0.03% and 0.05%) cause across the potentiometer 8 at exhalation tests. Let us denote these voltages by $V_{0.3}$ and $V_{0.5}$.

All feeding voltages of the apparatus are obtained from the voltage source 12. This may be composed of eight 1.5 V cells. The voltage from the voltage source 12 is supplied via a switch 14 as an input voltage to the regulating circuit 16. By means of the trimming potentiometer 18 the output voltage from the regulating circuit is adjustable to a predetermined accurate value, e.g., 5.00 V. This output voltage is then maintained constant, independent of the condition of the batteries. This is of greatest importance for the correct operation of the gas sensor.

The device according to the invention comprises two control circuits. The first control circuit is arranged to sense the output voltage from the regulating circuit 16 and indicate, when this voltage has decreased below a predetermined level. This control circuit is comprised of a Zener diode 20, the resistors 22 and 24, the potentiometer 26, the comparator device and the comparator 28, and the light emitting diode 32. If the regulating circuit 16 is set to supply an output voltage of 5.00 V ($\pm 0.05$ V), the transition point of the comparator 28 is adjusted by means of the potentiometer 26, so that the light emitting diode 32 is ignited, when the driving voltage from the regulating circuit 16 has decreased to 4.95 V. This is a warning to the user of the apparatus that the batteries should be replaced to ensure correct operation. At this control circuit the reference voltage is given by the Zener diode 20.

A second circuit is arranged to indicate, when the sensor is heated to operating temperature. This circuit is composed of two resistors 30 and 34, a comparison device or comparator 36, and a light emitting diode 40. A low voltage (e.g. 0.5 V) is applied to the negative input of the comparator 36. When the sensor has been heated to operating temperature and the voltage across the resistor 8 is reduced below the preset low voltage (e.g. 0.5 V) mentioned above, the light emitting diode 40 is ignited, thus indicating that the apparatus is ready to be used.

As the bend or knee voltage of the light emitting diode 32 is lower than the voltage of light emitting diode 40, these diodes can be connected to the driving voltage through a common resistor 38, connected between the driving voltage and the interconnected anodes of the light emitting diodes. The cathodes of the light emitting diodes are then connected directly to the respective comparator output. Normally, only the diode 40 is ignited. If the diode 32 is ignited, the diode 40 is extinguished or lights more feebly.

The apparatus according to the invention further comprises two additional comparator devices or comparators 42,44, wherein the output signal from the sensor 2 is compared with preset reference values. The voltage dividers 46,47 and 48,49 are rated so that from the midpoint connection the voltages $V_{0.3}$ and $V_{0.5}$ respectively, see above, are obtained, said voltages being supplied to one input of one comparator each 42,44. When the output voltage from the sensor, which is supplied to the second input of the comparators 42,44, exceeds $V_{0.3}$, the output signal from the comparator 42 is changed from "high" level to "low" level and at an output voltage of $V_{0.5}$ from the gas sensor the output signal of the comparator 44 is changed from "high" to "low".

In an alternative embodiment the voltage dividers 46,47 and 48,49 can be replaced by a potentiometer to allow individual trimming of the reference voltages for each sensor.

If the resistor of the sensor is $R_{0.3}$ and $R_{0.5}$ at the concentrations 0.3% and 0.5% respectively, and the potentiometer 8 is adjusted to the resistance $R_8 = \sqrt{R_{0.3} \cdot R_{0.5}}$ the voltage divider 46–47 is selected so that $V_{0.3} = \dfrac{U_{cc}}{1 + \sqrt{R_{0.3}/R_{0.5}}}$ and the voltage 48–49 so that $V_{0.5} = \dfrac{U_{cc}}{1 + \sqrt{R_{0.5}/R_{0.3}}}$ ($U_{cc}$ = the driving voltage)

If the quotient $R_{0.3}/R_{0.5}$ is constant for different specimens of the sensor, the voltages $V_{0.3}$ and $V_{0.5}$ will be equal for all sensors and the device can be calibrated by only varying the potentiometer 8.

In order to obtain a sufficiently accurate operation of the apparatus it is important that the reference voltage to the comparators 42 and 44 is taken from a constant voltage source via voltage dividers. Use of e.g. Zener diodes for this purpose, will not provide sufficient accuracy. The strong temperature drift of Zener diodes is another feature that renders them unsuitable as sources of reference voltages in the apparatus according to the invention.

A logic circuitry, composed of two SR flip-flops with inverted inputs, is connected to the outputs of the comparators 42,44. These flip-flops comprise two NAND gates each 50,52,54,56. The NAND gates are in their turn connected to light emitting diodes 58,60,62 which form indicator members of the apparatus.

The complete logic circuitry is preferably realized by means of an integrated circuit.

By the closing of a switch 64 the two SR flip-flops are reset to zero and only the light emitting diode 62 is ignited. However, if the output voltage from the sensor 2 exceeds $V_{0.3}$, the corresponding SR flip-flop is set to "1", the diode 62 is extinguished, and the diode 60 is ignited. If the output voltage from the sensor 2 exceeds $V_{0.5}$, the second SR flip-flop is set to "1", the diode 60 is extinguished, and the diode 58 is ignited. If the output voltage from the sensor is then reduced, this will not influence the SR flip-flops. They can only be reset to zero by closing of the switch 64.

An important feature of the apparatus according to the invention is that the logic circuitry is formed by TTL elements, whereby the output signals from the SR flip-flops can drive the three light emitting diodes 58,60,62 directly. Hereby an indication is obtained immediately without a special command signal and no separate voltage supply is required for the indicator members.

All comparators 28,36,42,44 comprised in the apparatus are conveniently embodied in an integrated circuit.

The light emitting diodes comprised in the apparatus are conveniently selected with different colours. Thus, for example, for the light emitting diode 32, a red light emitting diode can be selected, for the light emitting diode 40 a green light emitting diode, for the light emitting diode 58 a red light emitting diode, for the light emitting diode 60 a yellow light emitting diode, and for the light emitting diode 62 a green light emitting diode.

A list of components for a practical embodiment of the apparatus according to the invention is attached as Table 1.

Table 1

| List of components | | |
|---|---|---|
| Regulating cicuit 14 | LM 317 MP | |
| Comparators | 28,36,42,44 each ¼ IC2; IC 2 - LM 3302 | |
| NAND gates | 50,52,54,56 each ¼ IC3; IC 3 - SN 7400 | |
| Zener diode 20 | 3.3 V 0.5W | |
| Light emitting diode 32 | red | |
| Light emitting diode 40 | green | |
| Light emmitting diode 58 | red | |
| Light emitting diode 60 | green | |
| Light emitting diode 62 | green | |
| Switch 14 | Main switch | |
| Switch 64 | Press button | |
| Sensor 2 | Probe Figaro TGS 812 | |
| Voltage source 12 | Batteries (8 × 1.5 V) | |
| Potentiometer 18 | Trimming potentiometer | 470 ohm |
| Potentiometer 26 | Trimming potentiometer | 2.2 kohm |
| Potentiometer 8 | Trimming pontentiometer | 5 kohm |
| Resistor 66 | Resistor 5% | 1.2 kohm |
| Resistor 22 | " | 330 ohm |
| Resistor 24 | " | 1.3 kohm |
| Resistor 30 | " | 10 kohm |
| Resistor 38 | " | 330 ohm |
| Resistor 68 | " | 10 kohm |
| Resistor 70 | " | 10 kohm |
| Resistor 72 | " | 100 ohm |
| Resistor 74 | " | 2.2 kohm |
| Resistor 76 | " | 100 ohm |
| Resistor 34 | " | 1.2 kohm |
| Resistor 46 | Resistor 1% | 7.5 kohm |
| Resistor 47 | " | 9.1 kohm |
| Resistor 48 | " | 9.1 kohm |
| Resistor 49 | " | 7.5 kohm |

I claim:

1. An apparatus for determing the alcoholic content in blood, comprising a sensor disposed to produce a signal in response to the alcoholic content of exhaled air to which it is exposed from a test person, and at least two comparator devices for comparing said output signal with at least two preset reference values, a logic circuitry of TTL elements connected to the output of the comparator devices is arranged to actuate at least one light emitting diode of a plurality of light emitting diodes, said actuated light emitting diode being determined by the result of said comparison for indicating the alcoholic content, said logic circuitry comprising two SR flip-flops with inverted inputs, each of said flip-flops being composed of two NAND gates which are connected to three light emitting diodes in such a manner that a first light emitting diode is actuated when the output signal from the sensor is below the first reference value, the first light emitting diode is extinguished and the second light emitting diode is ignited when the output signal is between the first and second reference value, and the third light emitting diode is ignited and the second is extinguished when the output signal exceeds the second reference value.

2. The apparatus as claimed in claim 1, characterized in that the complete logic circuitry is realized by means of one integrated circuit.

3. The apparatus as claimed in claim 1, characterized in that the logic circuitry drives the light emitting diodes directly.

4. The apparatus as claimed in claim 1, characterized in that a voltage source is adapted to supply simultaneously the necessary feeding voltages to the sensor, the comparator devices, the logic circuitry, and the light emitting diodes.

5. The apparatus as claimed in claim 1, characterized in that the reference voltages required for the comparator devices are taken from a voltage source and are supplied to the comparator devices via voltage dividing resistors and potentiometers.

6. The apparatus as claimed in claim 5, characterized in that the apparatus is adapted to be calibrated by variation of the value of at least certain voltage dividing resistors.

7. The apparatus as claimed in claim 5, characterized in that the voltage supply is performed via a regulating circuit connected to the voltage source, said regulating circuit being adapted to supply a constant output voltage, independent of the condition of the batteries.

8. The apparatus as claimed in claim 7, characterized in that a first control circuit is disposed to sense the output voltage from the regulating circuit and indicate when said voltage has decreased below a predetermined level.

9. The apparatus as claimed in claim 8, characterized in that each one of the control circuits comprises a comparator device.

10. The apparatus as claimed in claim 1, characterized in that the reference voltages are adjusted so that the first reference value corresponds to an alcoholic content in the blood of 0.03% and the second reference value an alcoholic content of 0.05%.

11. The apparatus as claimed in claim 1, characterized in that the sensor is a gas sensor, the resistance of which is responsive to the alcoholic content in the exhaled air, to which it is exposed, and in that output signals from the sensors are obtainable across a resistor connected in series with the sensor.

12. The apparatus as claimed in claim 11 characterized in that the resistor connected in series with the sensor is a potentiometer, which is so arranged that the apparatus can be calibrated by means of said potentiometer alone.

13. The apparatus as claimed in claim 11, characterized in that a second control circuit is disposed to indicate when the sensor has been heated to operating temperature.

14. The apparatus as claimed in claim 3, characterized in that all comparator devices are comparators and in that they are formed by one integrated circuit.

* * * * *